(12) United States Patent
Vidlund et al.

(10) Patent No.: US 8,926,655 B2
(45) Date of Patent: *Jan. 6, 2015

(54) METHOD AND SYSTEM FOR SEALING PERCUTANEOUS PUNCTURES

(75) Inventors: Robert M. Vidlund, Forest Lake, MN (US); Douglas P. Killion, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 706 days.

This patent is subject to a terminal disclaimer.

(21) Appl. No.: 12/985,445

(22) Filed: Jan. 6, 2011

(65) Prior Publication Data

US 2011/0166595 A1     Jul. 7, 2011

Related U.S. Application Data

(60) Provisional application No. 61/282,236, filed on Jan. 6, 2010.

(51) Int. Cl.
*A61B 17/08* (2006.01)
*A61B 17/00* (2006.01)
*A61B 17/12* (2006.01)
*A61B 17/22* (2006.01)

(52) U.S. Cl.
CPC ....... *A61B 17/0057* (2013.01); *A61B 17/12136* (2013.01); *A61B 2017/00601* (2013.01); *A61B 2017/00623* (2013.01); *A61B 2017/00654* (2013.01); *A61B 2017/0065* (2013.01); *A61B 2017/00898* (2013.01); *A61B 2017/22042* (2013.01); *A61B 2017/22067* (2013.01)
USPC ........................................................ 606/213

(58) Field of Classification Search
CPC ................. A61B 17/0057; A61B 2017/00654; A61B 2017/00601; A61B 2017/00623; A61B 2017/00637
USPC .................................................. 606/213–215
See application file for complete search history.

(56) References Cited

U.S. PATENT DOCUMENTS

| 4,832,688 | A | * | 5/1989 | Sagae et al. | 604/509 |
| 5,419,765 | A | * | 5/1995 | Weldon et al. | 604/99.02 |
| 5,486,195 | A | * | 1/1996 | Myers et al. | 606/213 |
| 5,725,551 | A |   | 3/1998 | Myers et al. | |

(Continued)

FOREIGN PATENT DOCUMENTS

| JP | H11290460 A | 10/1999 |
| WO | 9222252 A1 | 12/1992 |
| WO | 9633658 A1 | 10/1996 |

OTHER PUBLICATIONS

PCT Partial International Search Report for PCT International Application No. PCT/US2013/027846 mailed Jul. 2, 2013 (2 pp.).

*Primary Examiner* — Gregory Anderson
(74) *Attorney, Agent, or Firm* — Holland & Hart

(57) ABSTRACT

A puncture closure device operable to seal closed a vessel puncture in a vessel. The puncture closure device includes a delivery member insertable through a tissue tract to the vessel puncture, a sealing material, and an expandable member. The sealing material is deliverable through the delivery member to the vessel puncture and configured to seal closed the vessel puncture from outside the vessel. The expandable member is positionable within the vessel through a vessel access distinct from the vessel puncture and is operable to temporarily seal closed the vessel puncture from within the vessel to restrict passage of the sealing material into the vessel.

18 Claims, 22 Drawing Sheets

(56) References Cited

U.S. PATENT DOCUMENTS

| | | | |
|---|---|---|---|
| 5,728,114 A * | 3/1998 | Evans et al. ............... | 606/148 |
| 5,728,132 A | 3/1998 | Van Tassel et al. | |
| 5,948,425 A * | 9/1999 | Janzen et al. ............... | 424/422 |
| 6,048,357 A * | 4/2000 | Kontos ....................... | 606/213 |
| 6,071,300 A | 6/2000 | Brenneman et al. ......... | 606/213 |
| 6,096,021 A * | 8/2000 | Helm et al. ................. | 604/509 |
| 6,371,975 B2 * | 4/2002 | Cruise et al. ................ | 606/214 |
| 6,537,299 B1 * | 3/2003 | Hogendijk et al. .......... | 606/213 |
| 6,994,686 B2 * | 2/2006 | Cruise et al. ................ | 604/82 |
| 7,331,981 B2 * | 2/2008 | Cates et al. ................. | 606/213 |
| 7,455,680 B1 * | 11/2008 | Ashby et al. ................ | 606/213 |
| 7,699,803 B2 | 4/2010 | Nayak et al. | |
| 8,333,787 B2 | 12/2012 | Pipenhagen et al. | |
| 2004/0267307 A1 * | 12/2004 | Bagaoisan et al. ........... | 606/213 |
| 2004/0267308 A1 * | 12/2004 | Bagaoisan et al. ........... | 606/213 |
| 2005/0065549 A1 | 3/2005 | Cates et al. | |
| 2005/0177189 A1 * | 8/2005 | Ginn et al. .................. | 606/213 |
| 2006/0085029 A1 * | 4/2006 | Brightbill ................... | 606/213 |
| 2007/0060950 A1 * | 3/2007 | Khosravi et al. ............. | 606/213 |
| 2008/0161849 A1 * | 7/2008 | Cates et al. ................. | 606/213 |
| 2008/0208213 A1 | 8/2008 | Benjamin et al. | |
| 2009/0171282 A1 | 7/2009 | Pipenhagen et al. | |
| 2009/0254110 A1 * | 10/2009 | Bagaoisan et al. ........... | 606/185 |
| 2010/0211000 A1 | 8/2010 | Killion et al. | |
| 2010/0274280 A1 | 10/2010 | Sawhney et al. | |

* cited by examiner

METHOD AND SYSTEM FOR SEALING PERCUTANEOUS PUNCTURES

CROSS-REFERENCE TO RELATED APPLICATION

This application claims the benefit of the filing date of U.S. Provisional Application No. 61/282,236, filed Jan. 6, 2010, and entitled METHOD AND SYSTEM FOR SEALING PERCUTANEOUS PUNCTURES, the disclosure of which is incorporated, in its entirety, by reference.

TECHNICAL FIELD

The present disclosure relates generally to a method and system for sealing, and more particularly, to methods and systems for sealing percutaneous punctures using, in certain embodiments, a multi-stage sealing material ejected into the puncture.

BACKGROUND

Certain medical procedures require the percutaneous puncturing of the body tissue of a patient to gain access to a cavity in the body to perform a medical procedure. One example of such a procedure is the puncturing of body tissue and a blood vessel wall to gain access to the interior of the vascular system of the patient. Such procedures that commonly require the percutaneous puncturing of a blood vessel wall are balloon angioplasty procedures, arteriography, venography, angiography and other diagnostic procedures that use blood vessel catheterization. Examples of other procedures requiring a puncture through body tissue into a cavity include laparoscopic surgery and other microscopic surgery techniques using a small incision.

In each of these procedures, it is necessary to close the incision or puncture through the body tissue after the surgical procedure. While there are a variety of prior art devices and techniques for closing such punctures, one primary problem is ensuring a complete seal of the puncture.

SUMMARY

One aspect of the present disclosure relates to a puncture closure device operable to seal closed a vessel puncture in a vessel. The puncture closure device includes a delivery member insertable through a tissue tract to the vessel puncture, a sealing material, and an expandable member. The sealing material is deliverable through the delivery member to the vessel puncture and configured to seal closed the vessel puncture from outside the vessel. The expandable member is positionable within the vessel through a vessel access distinct from the vessel puncture and is operable to temporarily seal closed the vessel puncture from within the vessel to restrict passage of the sealing material into the vessel.

The delivery member may include a first sheath and a sealing material delivery member insertable through the first sheath. The tissue puncture closure device may include a guide wire insertable into the vessel through the vessel access distinct from the vessel puncture. The expandable member may be configured to advance along the guide wire to the vessel puncture. The delivery member may include a first sheath, and the puncture closure device further includes a second sheath defining at least in part the vessel access distinct from the vessel puncture. The expandable member may be configured as an inflation balloon that is operable to block fluid flow through the vessel when expanded to temporarily seal closed the vessel puncture from within the vessel.

Another aspect of the present disclosure relates to a method of sealing a vessel puncture in a vessel. The method includes providing a tissue puncture closure device that includes a first portion having an inflatable member, and a second portion having a delivery member and a sealing material. The method also includes inserting the first portion into the vessel through an access point distinct from the vessel puncture, and positioning the inflatable member aligned with the vessel puncture, inflating the inflatable member to temporarily seal closed the vessel puncture from within the vessel, inserting the second portion through a tissue tract to the vessel puncture, delivering the sealing material to the vessel puncture with the delivery member, and sealing closed the vessel puncture with the sealing material from outside the vessel.

Inflating the inflatable member may restrict movement of the sealing material through the vessel puncture into the vessel. The delivery member may include a first sheath and a sealing material delivery member insertable through the first sheath. The method may include deflating the inflatable member and removing the first portion from the vessel after the sealing material seals closed the vessel puncture. The tissue puncture closure device may further include a guide wire, and the method includes inserting the guide wire into the vessel through the access point distinct from the vessel puncture and advancing the first portion along the guide wire.

A further aspect of the present disclosure relates to a vessel puncture closure device that includes a delivery device, an expandable member, a first sealing material, a guide wire, and a detachable sealing tip. The expandable member is configured to advance through the delivery device and through a vessel puncture in a vessel, and is operable to temporarily seal closed the vessel puncture from within the vessel. The first sealing material is deliverable through the delivery device to the vessel puncture to seal closed the vessel puncture from outside the vessel. The guide wire has a distal end portion. The detachable sealing tip is mounted to the distal end portion of the guide wire and is configured to detach from the guide wire within the first sealing material after removing the expandable member through the first sealing material.

The guide wire may extend through the expandable member. The guide wire may extend through the delivery device outside of the expandable member. The expandable member may include first and second balloon members, wherein the first balloon member is configured to restrict blood flow through a vessel and the second balloon member is configured to temporarily seal closed the vessel puncture from within the vessel. The expandable member may include first and second balloon members arranged within the vessel and overlapping the vessel puncture.

The delivery device may include a delivery tube comprising: an expandable member shaft lumen configured to receive the expandable member, a first stage sealing material delivery lumen configured to deliver the first sealing material, and a second stage sealing material delivery lumen configured to deliver a second sealing material. The second stage sealing material delivery lumen may include a one-way valve positioned at a distal end portion thereof that restricts flow of the first sealing material into the second stage sealing material delivery lumen. The vessel puncture closure device may include a mandrel positioned in the second stage sealing material delivery lumen and removable after the first sealing material has been delivered through the first stage sealing material delivery lumen and before delivering the second sealing material through the second stage sealing material delivery lumen. The delivery device may include a bypass channel formed between the second stage sealing material delivery lumen and the expandable member shaft lumen, wherein the expandable member seals closed the bypass channel to restrict flow of the second sealing material until after the expandable member is retracted proximal of the bypass channel.

Another aspect of the present disclosure relates to a method of closing a puncture in a vessel. The method includes providing a puncture closure device including a delivery device, an expandable member, a first sealing material, a guide wire, and a detachable sealing tip mounted to a distal end of the guide wire. The method also includes advancing a delivery device to the puncture, advancing the expandable member through the delivery device and puncture into the vessel, temporarily sealing closed the puncture with the expandable member from within the vessel, delivering the first sealing material through the delivery device to the puncture to seal closed the puncture from outside the vessel, removing the expandable member through the first sealing material, and depositing the detachable sealing tip within the first sealing material.

The method may also include advancing the guide wire through the vessel puncture to position the detachable sealing tip within the vessel before advancing the expandable member through the delivery device and into the vessel. Depositing the detachable sealing tip within the first sealing material may include retracting the guide wire through the first sealing material after removing the expandable member through the first sealing material. Depositing the detachable sealing tip may include advancing the guide wire through the delivery device to the first sealing material after removing the expandable member through the first sealing material.

The method may further include delivering a second sealing material through the delivery device to the first sealing material after removing the expandable member through the first sealing material. The delivery device may include at least first and second lumens, delivering the first sealing material may include advancing the first sealing material through the first lumen, and delivering the second sealing material may include advancing the second sealing material through the second lumen. The expandable member may include first and second balloon members, and the method may include operating the first balloon to temporarily seal closed the vessel puncture, and operating the second balloon member to temporarily stop blood flow through the vessel.

Another aspect of the present disclosure relates to a method of sealing closed a vessel puncture in a vessel. The method includes delivering a first sealing material to an outer surface of the vessel to sealing closed the vessel puncture, depositing a detachable sealing member within the delivered first sealing material, and delivering a second sealing material to the delivered first sealing material to at least partially cover the first sealing material.

The method may further include forming a channel through the delivered first sealing material, and depositing the detachable sealing member includes positioning the detachable sealing member in the channel. The first and second sealing materials may comprise different material properties, and delivering the first sealing material includes ejecting the first sealing material in a liquid, gel or semi-solid state. The method may also include temporarily sealing closed the vessel puncture from within the vessel prior to delivering the first sealing material. Depositing the detachable sealing member may occur prior to delivering the second sealing material. Depositing the detachable sealing member may include retracting the detachable sealing member from within the vessel, through the vessel puncture, and into the first sealing material.

The foregoing and other features, utilities, and advantages of the invention will be apparent from the following detailed description of the invention with reference to the accompanying drawings.

BRIEF DESCRIPTION OF THE DRAWINGS

Reference will now be made in detail to exemplary embodiments illustrated in the accompanying drawings. Wherever possible, the same reference numbers will be used throughout the drawings to refer to the same or like parts.

DETAILED DESCRIPTION

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The terms proximal and distal are used herein to refer to the relative positions of the components of the exemplary sealing system 10. When used herein, proximal refers to a position relatively closer to the exterior of the body or closer to the surgeon using the sealing system 10. In contrast, distal refers to a position relatively further away from the surgeon using the sealing system 10 or closer to the interior of the body.

Figure 1:
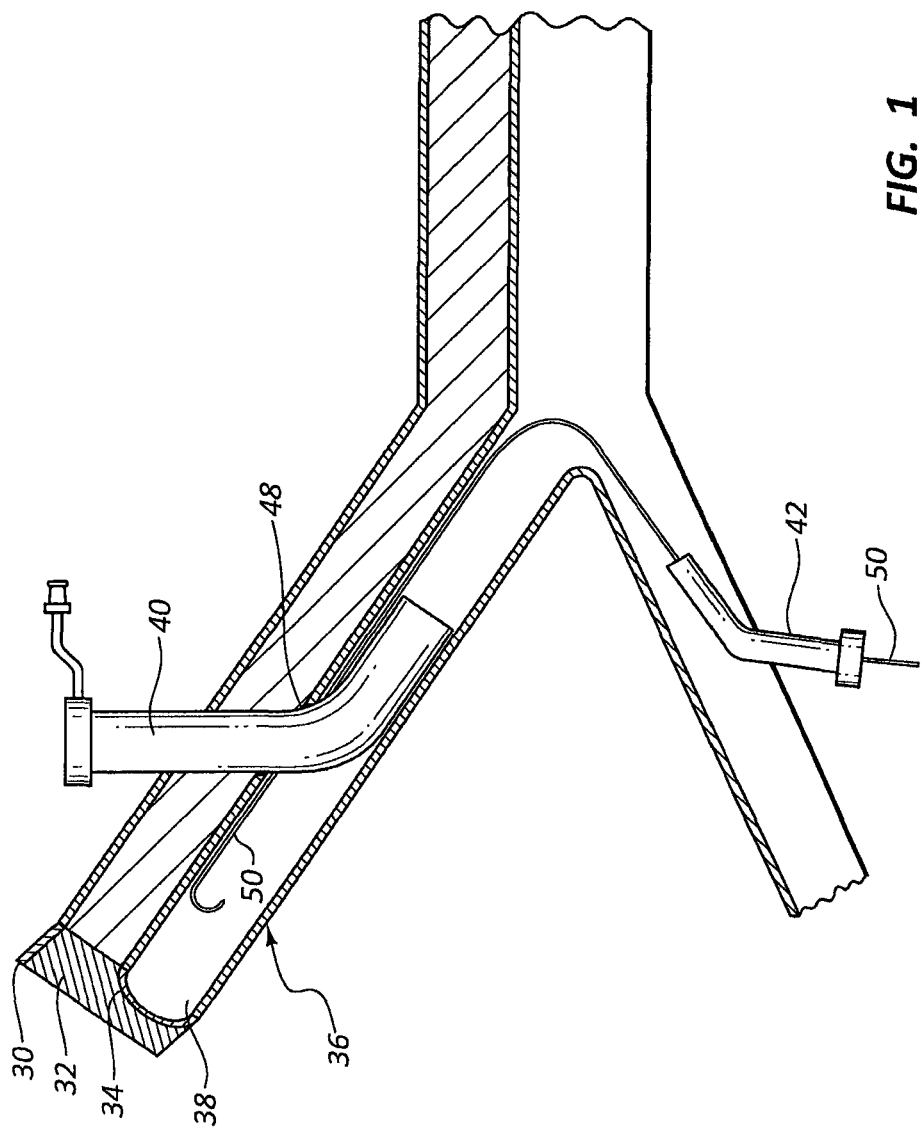
FIG. 1 illustrates an exemplary embodiment showing a primary guide sheath, a secondary guide sheath, and a guide wire within a vessel.
Figure 2:
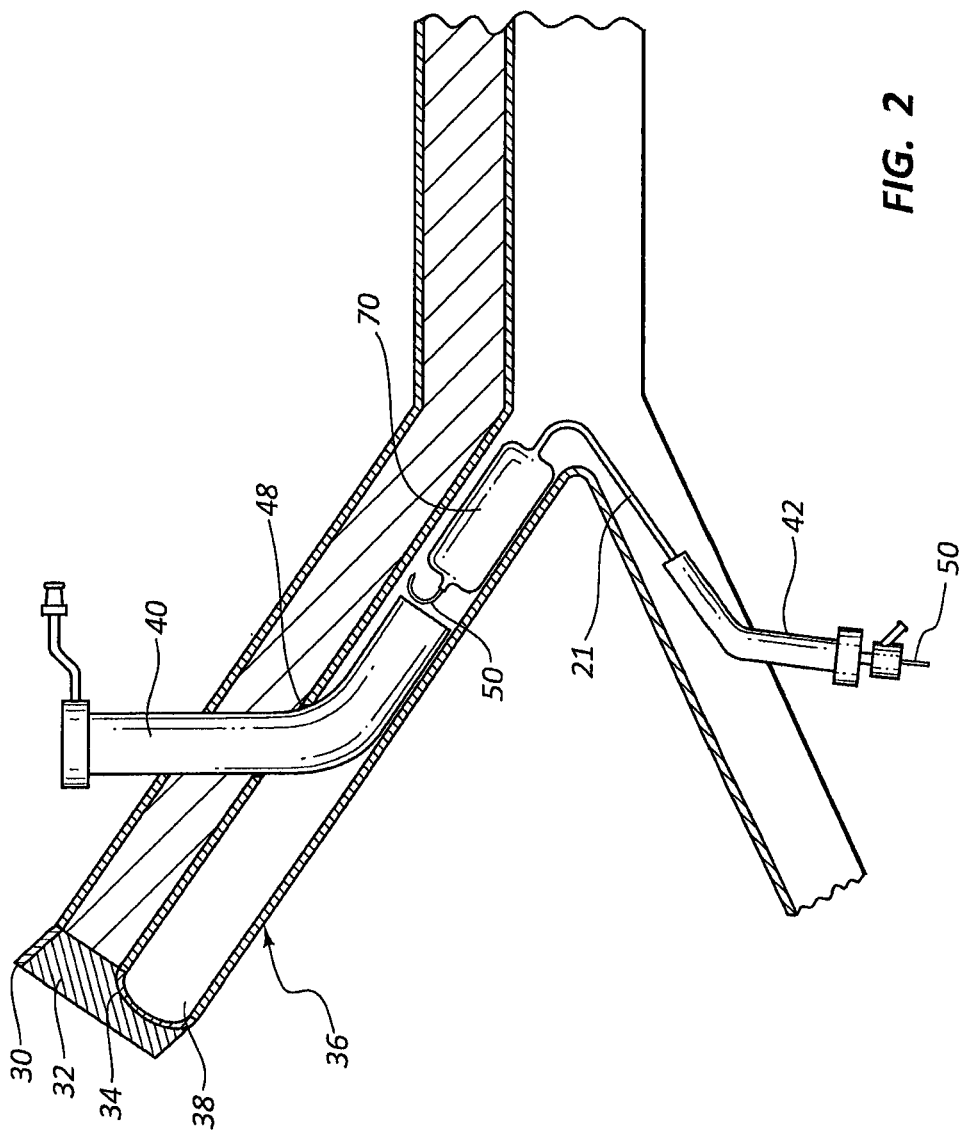
FIG. 2 illustrates the embodiment of FIG. 1 with an expandable member positioned distal to the primary guide sheath.
Figure 3:
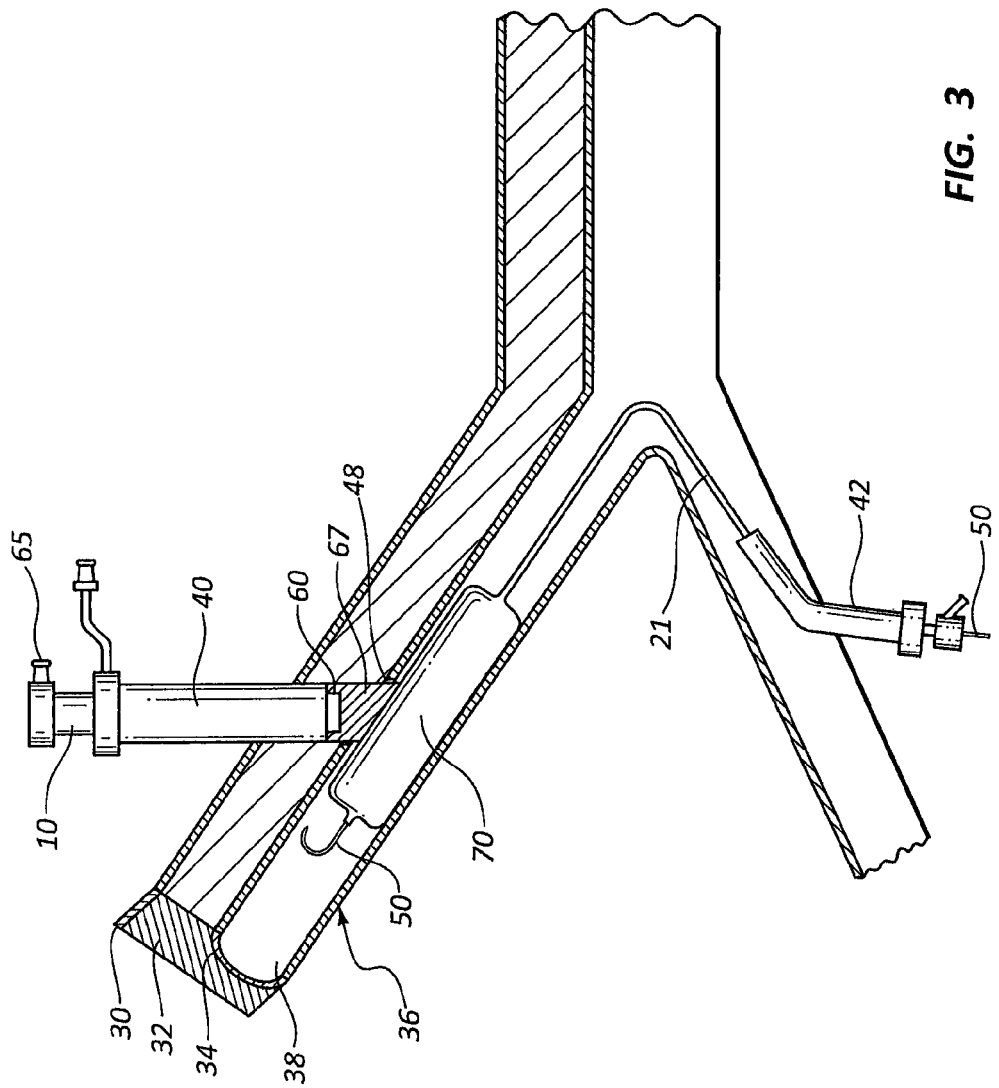
FIG. 3 illustrates an exemplary embodiment with an expandable member covering a puncture site internal a blood vessel, a sealing system inserted into a guide sheath, and sealing material delivered within a tissue tract.

An exemplary embodiment of sealing system 10 is illustrated being used to seal a percutaneous puncture 48 made through the skin 30, body tissue 32, and the wall 34 of a blood vessel 36 as an incident to a medical procedure (see FIGS. 1-3). Typically, the blood vessel 36 is a femoral artery in the groin region with a relatively large vessel passage or lumen 38 to facilitate easier locating of the blood vessel 36 and permitting a sufficiently large puncture to be made through the wall 34 thereof to carry out the procedure. Medical procedures that are typically performed through such a puncture are angioplasty and other procedures that pass a catheter or other type of probe into and along the blood vessel lumen 38. When such a procedure is performed, an initial percutaneous puncture with an appropriate needle is made from the patient's skin 30 through the tissue 32, and the blood vessel wall 34 into the blood vessel lumen 38. A guide wire is installed through the percutaneous puncture. The needle is then removed leaving the guide wire in place and an introducer guide sheath 42, which may be tapered, is installed over the guide wire to enlarge the puncture so as to permit easier access to the blood vessel 36.

A second percutaneous puncture 48 may be made with an appropriate needle from the patient's skin 30 through the tissue 32 and the blood vessel wall 34 into the blood vessel lumen 38. Guide sheath 40 may be inserted through the percutaneous puncture 48. The guide sheath 40 serves to keep the passage open and prevent further damage to the tissue 32 and skin 30 around the passage during the medical procedure. The guide sheath 40, assists in the installation of the sealing system 10 as will be described in further detail herein. The guide sheath 42 assists in the installation of guide wire 50 and temporary sealing component 21. The temporary sealing component 21 may be placed in position using a guide wire 50 or tracked into position without the use of guide wire 50.

Figure 4:
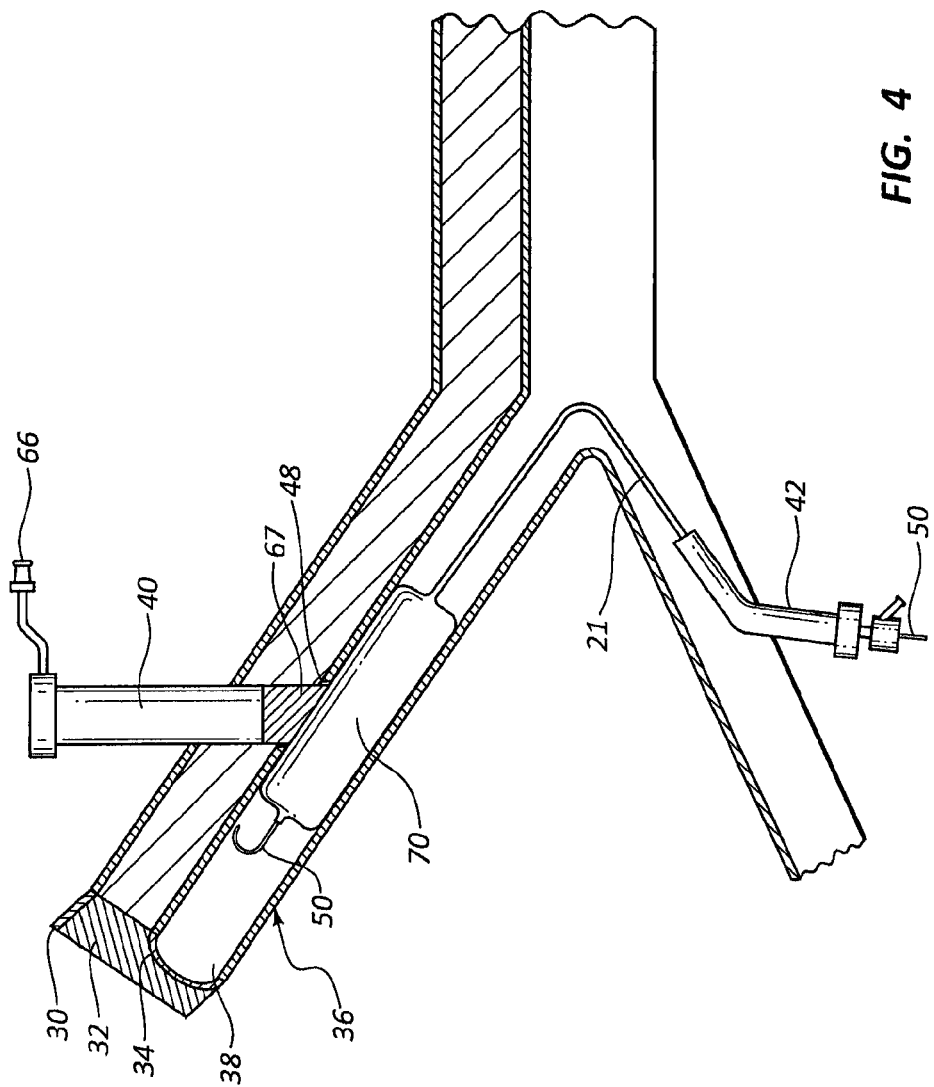
FIG. 4 illustrates an exemplary embodiment with an expandable member covering a puncture site internal a blood vessel, sealing material delivered through a guide sheath, and sealing material delivered within a tissue tract.

Referring to FIG. 4, an exemplary embodiment includes the guide sheath 40 acting as the sealing material delivery component, and sealing material 67 is delivered through guide sheath 40 and positioned at percutaneous puncture 48. Temporary sealing component 21 is inserted through guide sheath 42 and tracked over guide wire 50. The tamponading member 70 (also referred to herein as a balloon, balloon member, or expandable member) is positioned distal to percutaneous puncture 48 and is expanded. Expanding tamponading member 70 with the blood vessel 36 temporarily seals the percutaneous puncture and prevents blood from traveling out though percutaneous puncture 48. Also, expanding tamponading member 70 creates a bridge over the percutaneous puncture 48 so that sealing material 67 may be delivered through guide sheath 40 and positioned over percutaneous puncture 48. Once sealing material 67 is positioned over percutaneous puncture 48, the tamponading member 70 is deflated and removed from guide sheath 42. In some arrangements, the sealing material is permitted to cure or expand prior to removal of tamponading member 70. Guide sheath 40 is removed from tissue 32 and patient's skin 30. The percutaneous puncture is completely sealed by sealing material 67.

Figure 5:
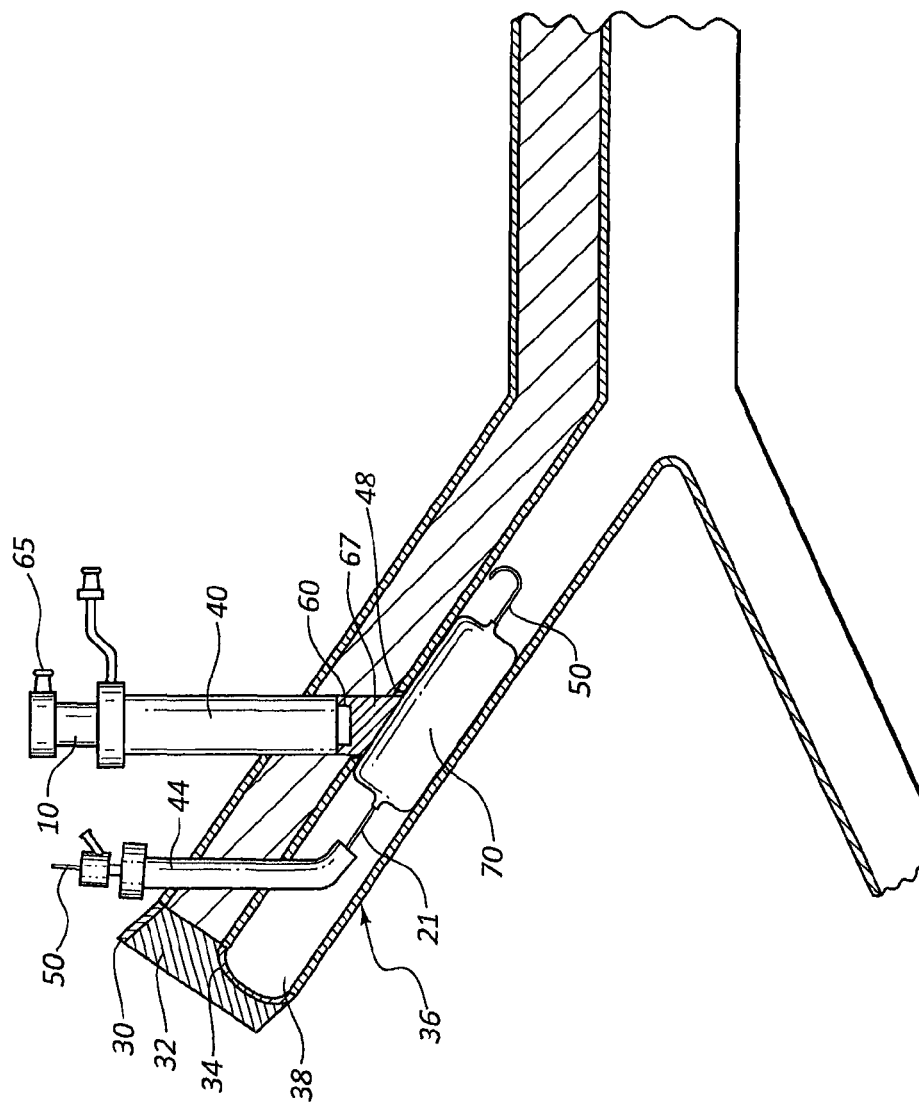
FIG. 5 illustrates an exemplary embodiment with an expandable member entering a patient from an alternative location and covering a puncture site internal a blood vessel, a sealing system inserted into a guide sheath, and sealing material delivered within a tissue tract.

Referring to FIG. 5, an exemplary embodiment includes sealing system 10 inserted through the guide sheath 40. A different guide sheath 44 is inserted distal to guide sheath 40. Guide sheath 44 assists in the installation of guide wire 50 and temporary sealing component 21. Temporary sealing component 21 is inserted through guide sheath 44 and tracked over guide wire 50. The tamponading member 70 of temporary sealing component 21 is positioned distal to percutaneous puncture 48 and is expanded. Expanding tamponading member 70 temporarily seals the percutaneous puncture and prevents blood from traveling out though percutaneous puncture 48. Also, expanding tamponading member 70 creates a bridge over the percutaneous puncture 48 so that sealing material 67 may be delivered through sealing system 10 and positioned over percutaneous puncture 48.

Once sealing material 67 is positioned and cured over percutaneous puncture 48, the tamponading member 70 is deflated. Sealing system 10 is removed from guide sheath 40. The temporary tamponading member 70 is left deflated distal to percutaneous puncture 48 and the success of the closure is monitored. When closure is successful, guide sheath 40 and sealing system 10 are removed from patient's skin 30 and guide sheath 44 is removed from patient's skin 30. The percutaneous puncture 48 is completely sealed by sealing material 67.

If closure is not successful, the temporary tamponading member is re-inflated and blood flow through the percutaneous puncture is stopped. The sealing system 10 may be reinserted through guide sheath 40, or alternatively, a second sealing system 10 may be inserted through the guide sheath 40. A second delivery of sealing material 67 may be delivered creating a complete closure. Guide sheath 40 and sealing system 10 are removed from patient's skin 30 and guide sheath 44 and temporary sealing component are removed from tissue 32 and patient's skin 30. The percutaneous puncture 48 is completely sealed by sealing material 67.

The delivery tube 60 may be manufactured from any number of materials without departing from the scope of the present disclosure. In one embodiment, the delivery tube 60 is made of a polymeric material such as high-density polyethylene (HDPE), Nylon or polyamide.

Referring to FIGS. 3 and 5, an exemplary embodiment of the sealing system 10 is illustrated depositing the first stage of sealing material 67 in the percutaneous puncture 48. A first stage of sealing material 67 may be mixed outside of the sealing system 10, for example, in a double-barrel syringe (not shown). The mixed first stage of sealing material 67 is then injected into first sealing material port 65 and flows through delivery tube 60. As illustrated in FIGS. 3 and 5, the distal end of delivery tube 60 may be positioned proximate to the blood vessel wall 34. The first stage sealing material 67 exits the delivery tube 60 at the distal end and is deposited in the region immediately proximate to the blood vessel wall 34 creating a seal where the percutaneous puncture 48 passed through the blood vessel wall 34.

Figure 6:
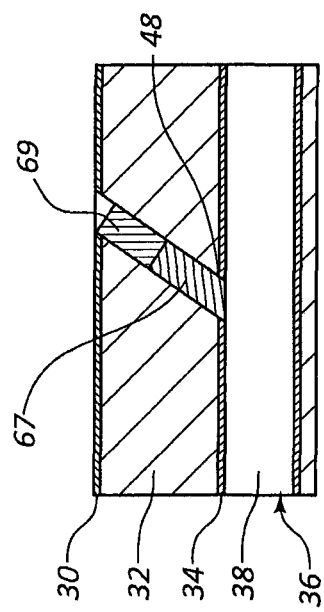
FIG. 6 illustrates an exemplary embodiment of sealing material positioned over a percutaneous puncture.
Figure 7:
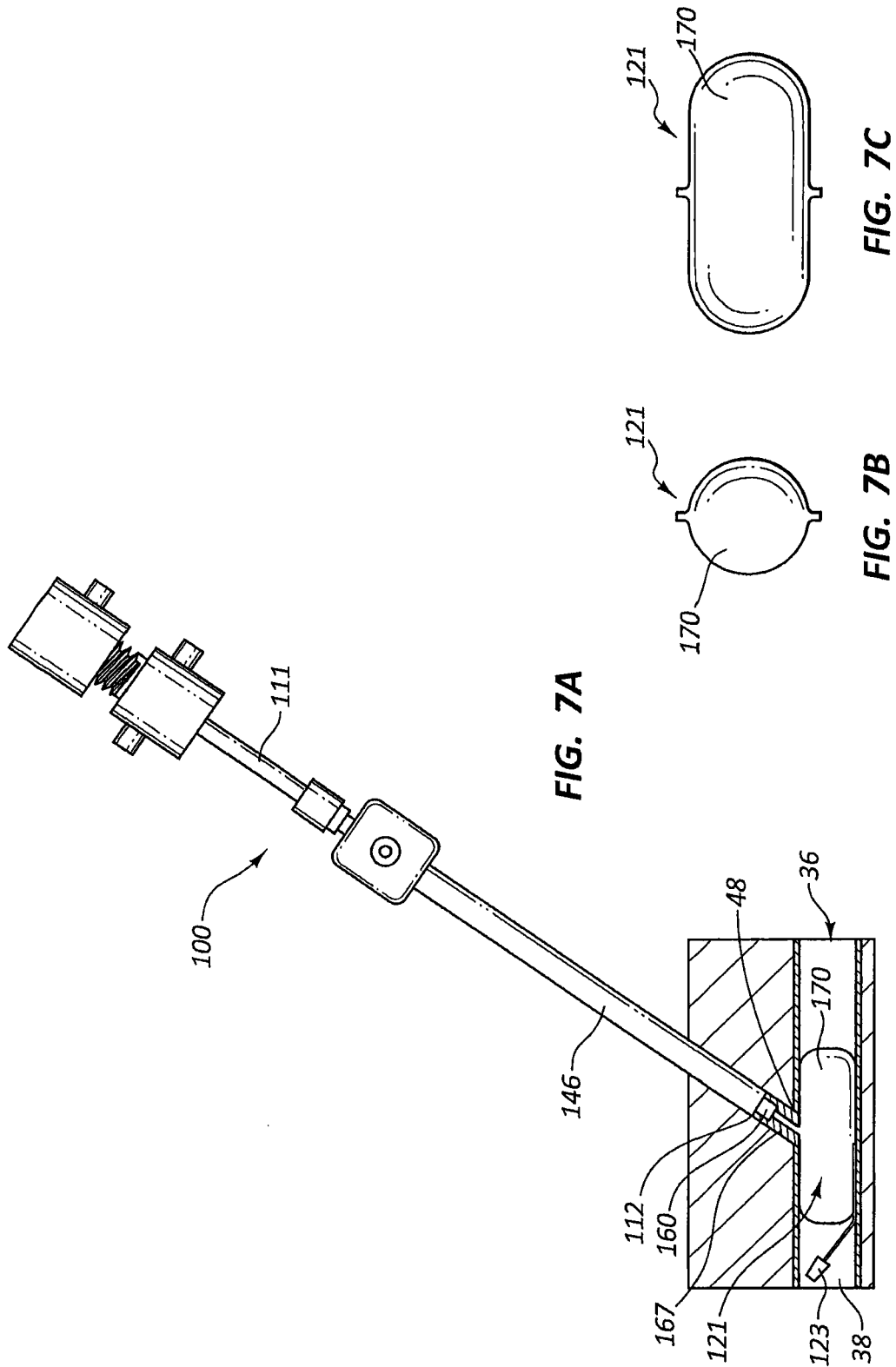
FIG. 7A illustrates an exemplary embodiment of an expandable member positioned within a blood vessel and expanded more in one direction than the other.
FIGS. 7B-C illustrate end and side views, respectively, of the expandable member of FIG. 7A.

Referring to FIG. 4, an exemplary embodiment using a guide sheath 40 is illustrated depositing the first stage of sealing material 67 in the percutaneous puncture 48. The first stage of sealing material 67 may be mixed outside of guide sheath 40, for example, in a double-barrel syringe (not shown). The mixed first stage of sealing material 67 is then injected into first sealing material port 66 and flows through guide sheath 40. As illustrated in FIG. 4, the distal end of guide sheath 40 has been positioned proximate to the blood vessel wall 34. The first stage sealing material 67 exits the guide sheath 40 at the distal end and is deposited in the region immediately proximate to the blood vessel wall 34 to create a seal where the percutaneous puncture 48 passed through the blood vessel wall 34. FIG. 6 shows a complete closure with sealing material 67 covering the percutaneous puncture 48.

A second stage sealing material 69 may be deposited on the first state sealing material 67. The second stage sealing material 69 may be delivered using the ports 65, 66 or other ports or access openings of the sealing system 10.

The sealing material used in the first and second stages of sealing the percutaneous puncture 48 may be any of a number of different biocompatible materials as long as the material has the capability of maintaining a seal in the percutaneous puncture 48. For example, the sealing material may be a liquid or gel that is flowable. The sealing material may be a combination of liquid and solid materials, for example, the first stage sealing material may be a preformed solid and the second stage sealing material 69 may be a flowable material. In yet another embodiment, the sealing material may be a compound that is mixed either prior to inserting the sealing material into the sealing material delivery tube 60 or guide sheath 46, or that is mixed as it passes through the sealing material delivery tube 60. The sealing material may be a material that bonds the body tissue 32 at the percutaneous puncture 48 together such as, for example and without limitation, a biocompatible adhesive. In one embodiment, the sealing material is a polyethylene glycol based adhesive provided in a flowable state. The first and second sealing materials (as well as the detachable sealing tips disclosed herein) may have different compositions and be provided in different states (e.g., liquid, gels, solid, or semi-solid or semi-gel states).

Referring to FIGS. 7A-19, various sealing system embodiments are shown inserted into a blood vessel lumen 38 through an introducer guide sheath 146. As described in greater detail below, an expandable tamponading member of a temporary sealing component is expanded within the blood vessel lumen 38. The sealing systems and guide sheath 146 are then retracted, and the expandable tamponading member of the temporary sealing component serves to temporarily seal the interior end of a percutaneous puncture 48 into the blood vessel lumen 38.

While the temporary sealing component is in the proper retracted position for sealing the percutaneous puncture 48 in the blood vessel 36, a sealing material delivery component is located in the percutaneous puncture 48 and proximate to a punctured blood vessel wall 34. When the sealing material delivery component is located proximate to the punctured blood vessel wall 34, a first stage of the sealing material for sealing the percutaneous puncture 48 may be injected through the sealing material delivery component. After the first stage of sealing material is installed, the expandable tamponading member may be contracted and the temporary sealing component is removed. A bioabsorbable tip may be left behind (e.g., see FIG. 19). A second stage of sealing material may then be installed in the percutaneous puncture 48 as the sealing material delivery arrangement is removed (e.g., see FIG. 19).

Referring further to FIG. 7A, a sealing system 100 includes an exemplary embodiment of a temporary expandable member 121 having a balloon 170 that expands unequally in different directions. FIGS. 7B and 7C illustrate the balloon shape from an axial direction (FIG. 7B) and from a lateral direction (FIG. 7C). As the balloon 170 is inflated, a short axis of the balloon may become generally circular and take the shape of the blood vessel 36. The balloon 170 may take on an elongated shape that fills the blood vessel 36 down a length of the blood vessel 36 along a long axis of the balloon 170. The more pressure that is applied to the balloon 170 the more the balloon 170 continues to elongate. The ability for the balloon 170 to elongate and bridge the opening of the percutaneous puncture 48 may be important when closing large bore percutaneous punctures 48.

The expandable member 121 may be directed along a support wire 161 into the blood vessel lumen 38. The expandable member 121 may be advanced through a delivery device that includes a guide sheath 146 and a delivery tube 160. A first stage of sealing material 167 may be positioned in the tissue tract 32 to seal closed the percutaneous puncture 48. A sealing tip 123 may be left behind in the sealing material 167 upon removal of the expandable member 121 from the sealing material 167, or of the sealing system 100 from the blood vessel 36 generally.

Figure 8:
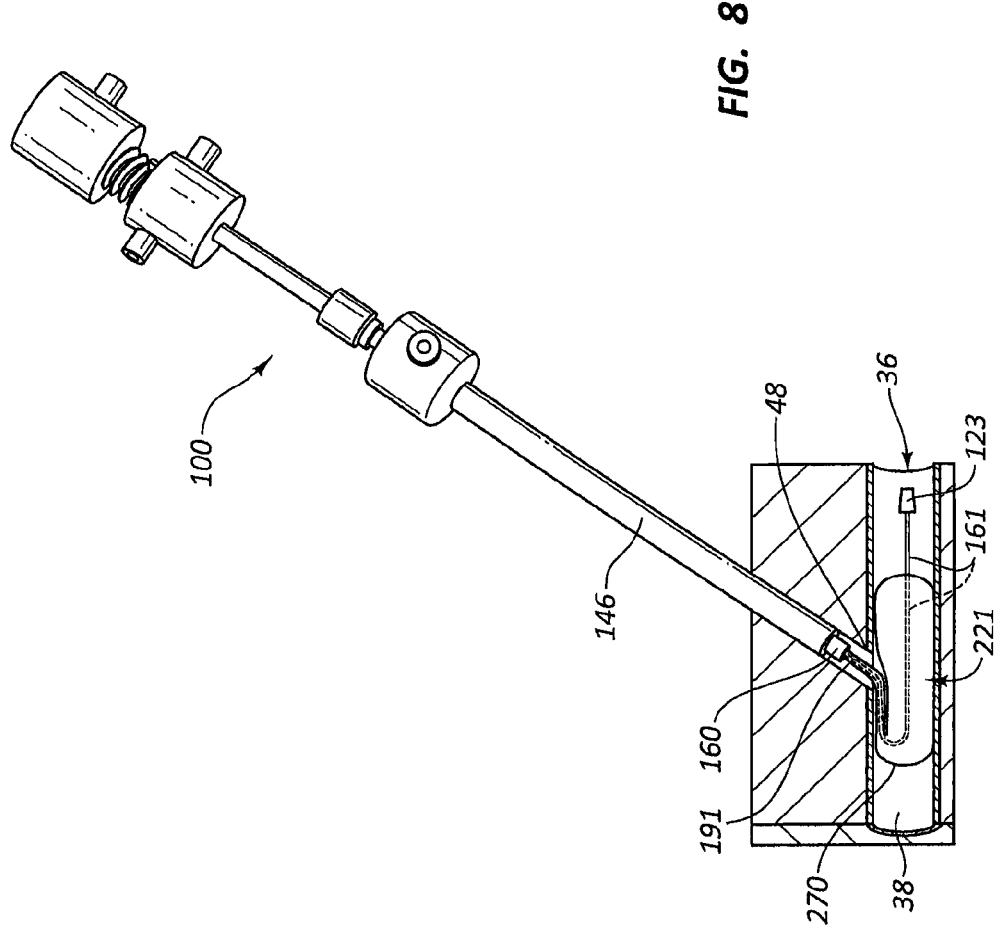
FIG. 8 illustrates an exemplary embodiment of an expandable member positioned within a blood vessel and overlapping itself.

Referring to FIG. 8, the sealing system 100 includes another exemplary embodiment of a temporary expandable member 221 that includes an overlapping balloon 270. The balloon 270 is folded into a position overlapped on itself. Balloon 270 is inflated to temporarily seal the percutaneous puncture 48. The balloon 270 may take an initial shape by partially inflating. The partially inflated temporary expandable member 221 may then be pulled into a position distal to the percutaneous puncture 48. Partially expanding the expandable member 221 may help track the expandable member 221 into position and help identify the location of the percutaneous puncture 48.

A support wire 161 may be pre-shaped to help maintain the shape of the expandable member 221. The shape of support wire 161 and expandable member 221 may act as a hook to help position the expandable member 221 distal of the percutaneous puncture 48. The temporary positioning may help the user know when the expandable member 221 is in a proper location prior to fully inflating the expandable member 221.

A tube 191 may act as a support member within the sealing material 167. During the removal of the temporary expandable member 121, the channel within the sealing material 167 may become compromised or damaged. Tube 191 may provide support and protection for the sealing material while the temporary expandable member is withdrawn through tube 191.

Figure 9:
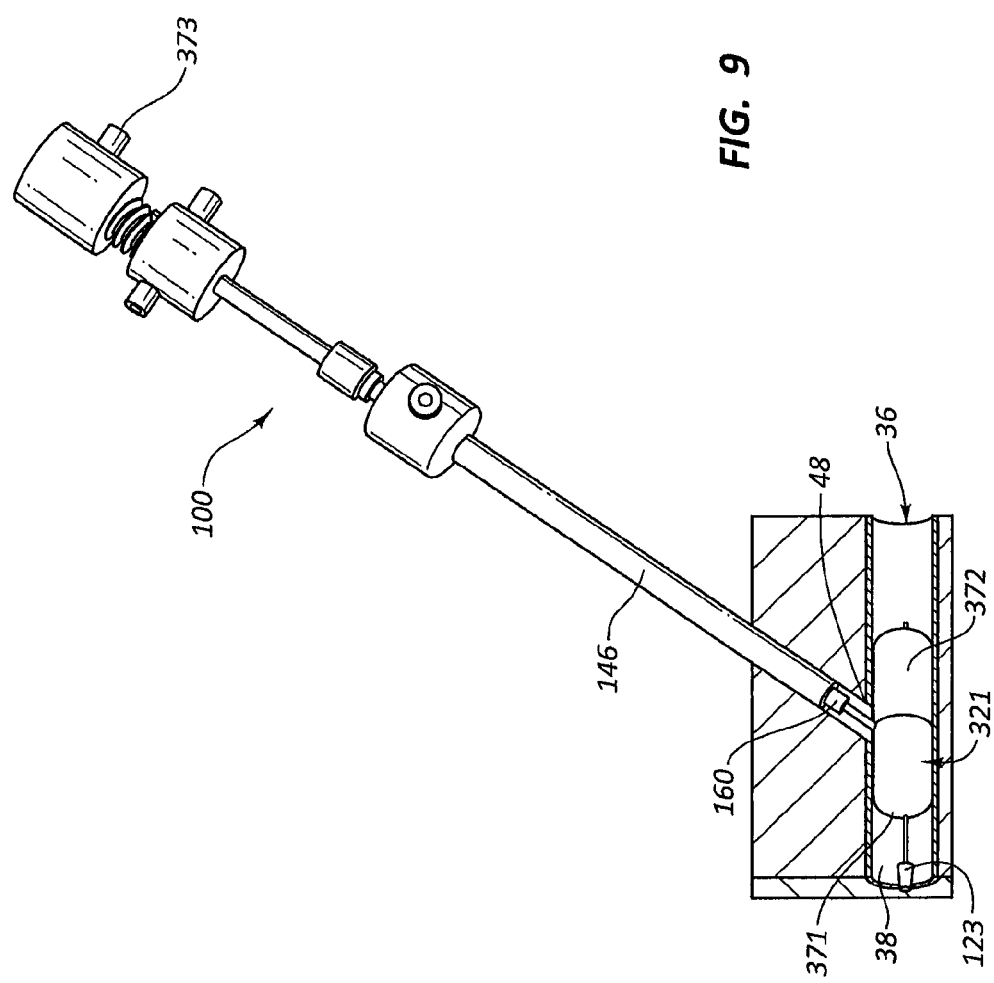
FIG. 9 illustrates an exemplary embodiment of two expandable members positioned within a blood vessel.

Referring to FIG. 9, the sealing system 100 includes another exemplary embodiment of a temporary expandable member 321 having two balloons 371, 372. The two balloons 371, 372 may be inflated together using inflation port 373, or may be inflated independently using two separate ports (not shown). The two balloons 371, 372 may create a temporary seal or bridge over percutaneous puncture 48. The balloons 371, 372 may be arranged coaxially. The balloons 371, 372 may be arranged side-by-side and in contact with each other.

Figure 10:
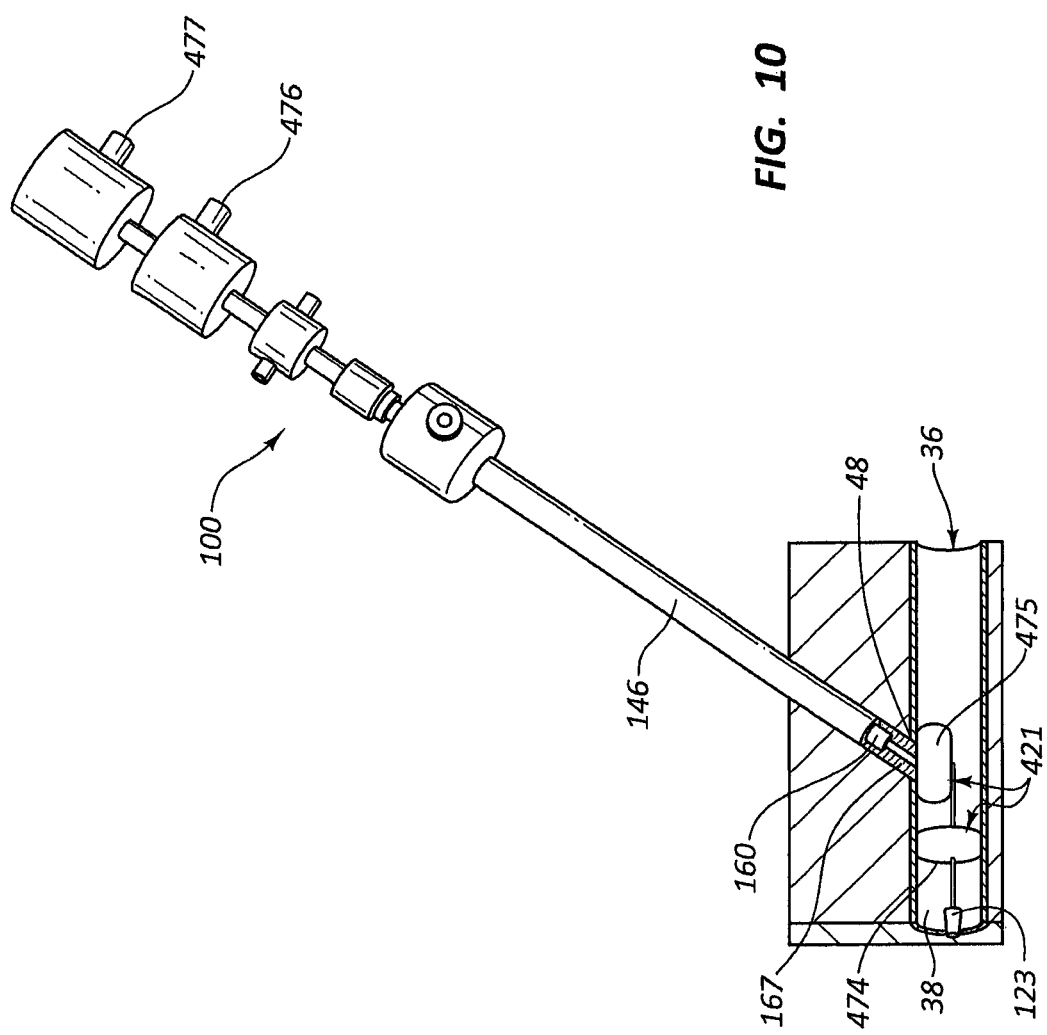
FIG. 10 illustrates an exemplary embodiment of two expandable members positioned within a blood vessel that are positioned and activated independently.

Referring to FIG. 10, the sealing system 100 includes another exemplary embodiment of a temporary expandable member 421 that includes two balloons 474, 475. Balloon 474 is positioned and operable to stop blood or reduce arterial pressure at the site of the percutaneous puncture 48. Balloon 475 is positioned and operable to seal the percutaneous puncture 48 and create a bridge or plug to restrict movement of for the first stage sealing material 167 into blood vessel 36. Balloons 474, 475 may be movable independently, or may move in tandem. Balloon 474 may be inflated using port 476. Balloon 475 may be inflated using port 477. In some arrangements, balloons 475, 476 may be inflated through a common port. Temporary expandable members 474, 475 may have various shapes such as, for example, the shape of a disc.

Figure 11:
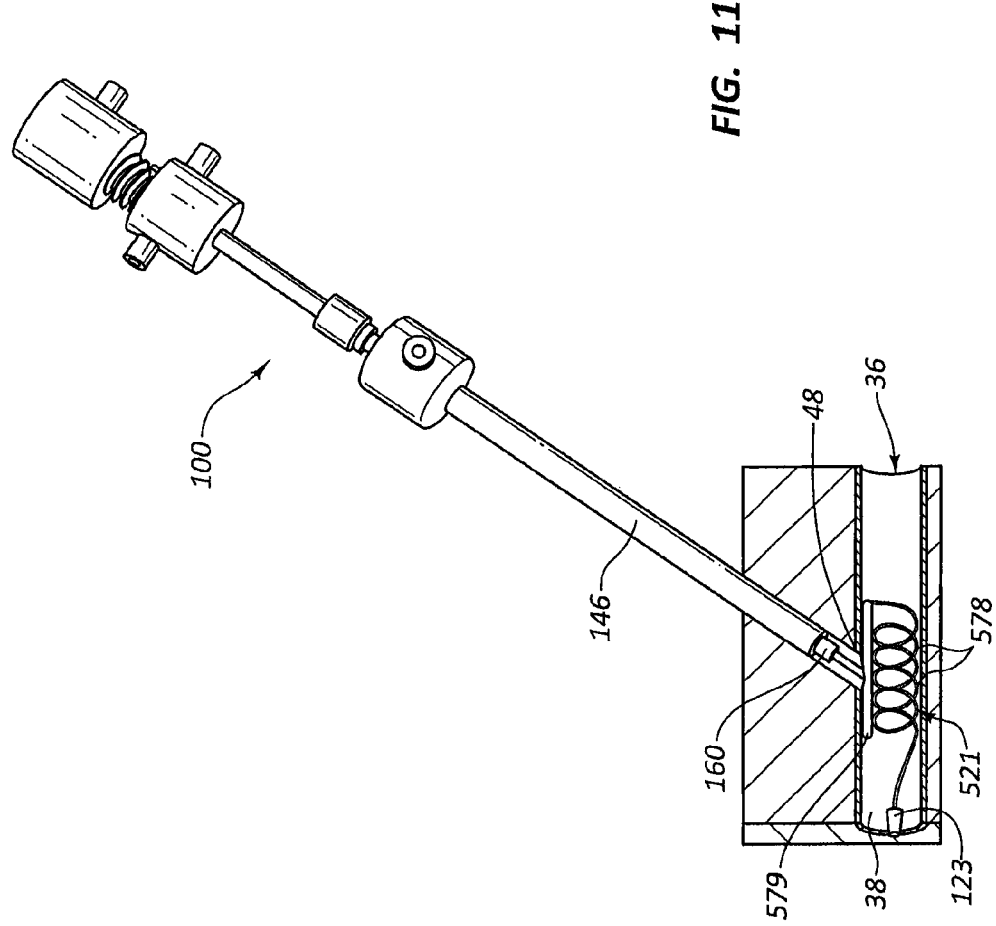
FIG. 11 illustrates an exemplary embodiment of an expandable member positioned within a blood vessel with a disc and wire support structure.

Referring to FIG. 11, the sealing system 100 includes another exemplary embodiment of a temporary expandable member 521 having a disc 579 with a wire support structure 578. The wire support structure 578 is expandable within blood vessel 36. For example, the wire support structure 578 may be formed of a self-expanding material. The expanded wire support structure 578 may be used to move a disc 579 up against percutaneous puncture 48. The support wires may comprise a material such as, for example, nickel titanium or Nitinol, and the disc may comprise a polymer such as, for example, urethane, silicone, PET, or Polyethylene.

Figure 12:
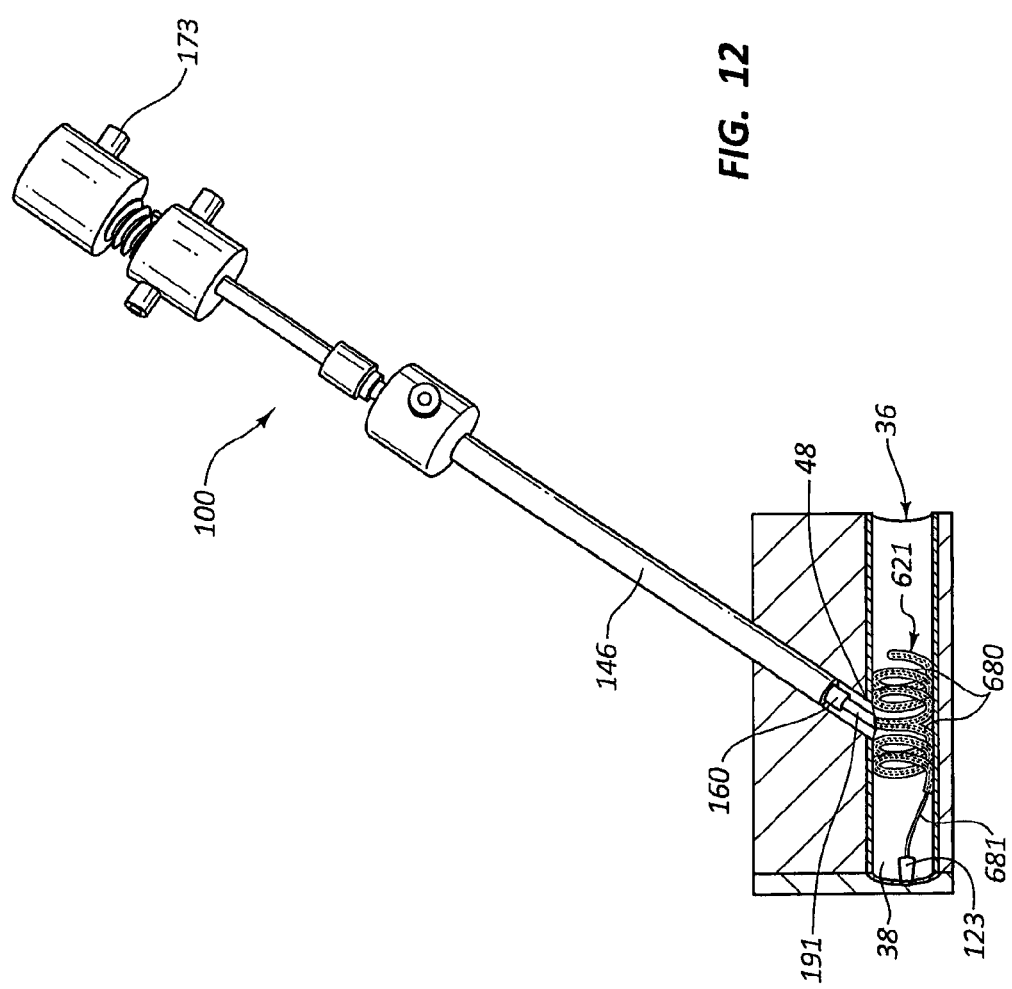
FIG. 12 illustrates an exemplary embodiment of an expandable member positioned within a blood vessel with an inflatable balloon extending over a wire structure.

Referring to FIG. 12, the sealing system 100 includes another exemplary embodiment of a temporary expandable member 621 having a spiral shaped shape memory (e.g., Nitinol) wire 681 with a balloon 680 positioned over the spiral shaped wire 681. The spiral shaped wire 681 releases out through tube 191 and is positioned over percutaneous puncture 48. The balloon tubing 680 when inflated may create a seal over the percutaneous puncture 48. The balloon tubing 680 may be inflated using port 173.

Figure 13:
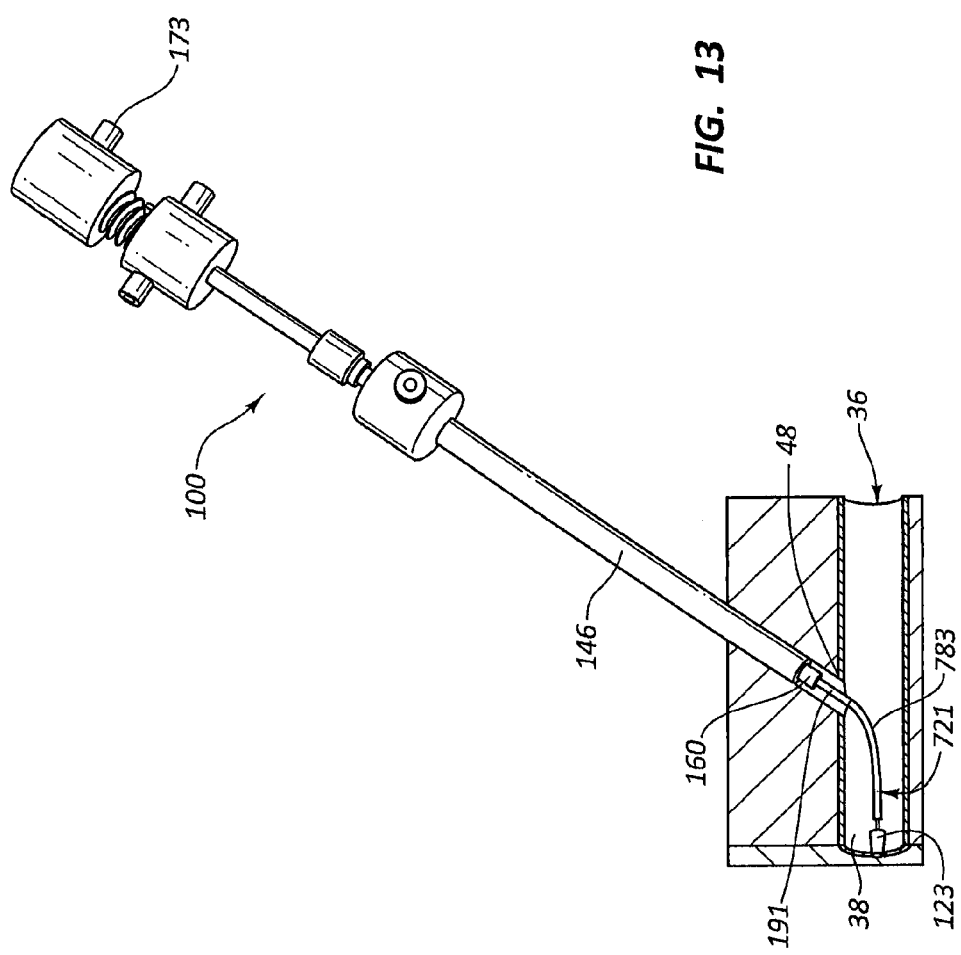
FIGS. 13 and 14 illustrate an exemplary embodiment of an expandable member positioned within a blood vessel and that pro-lapses and continues to elongate at different pressures
Figure 14:
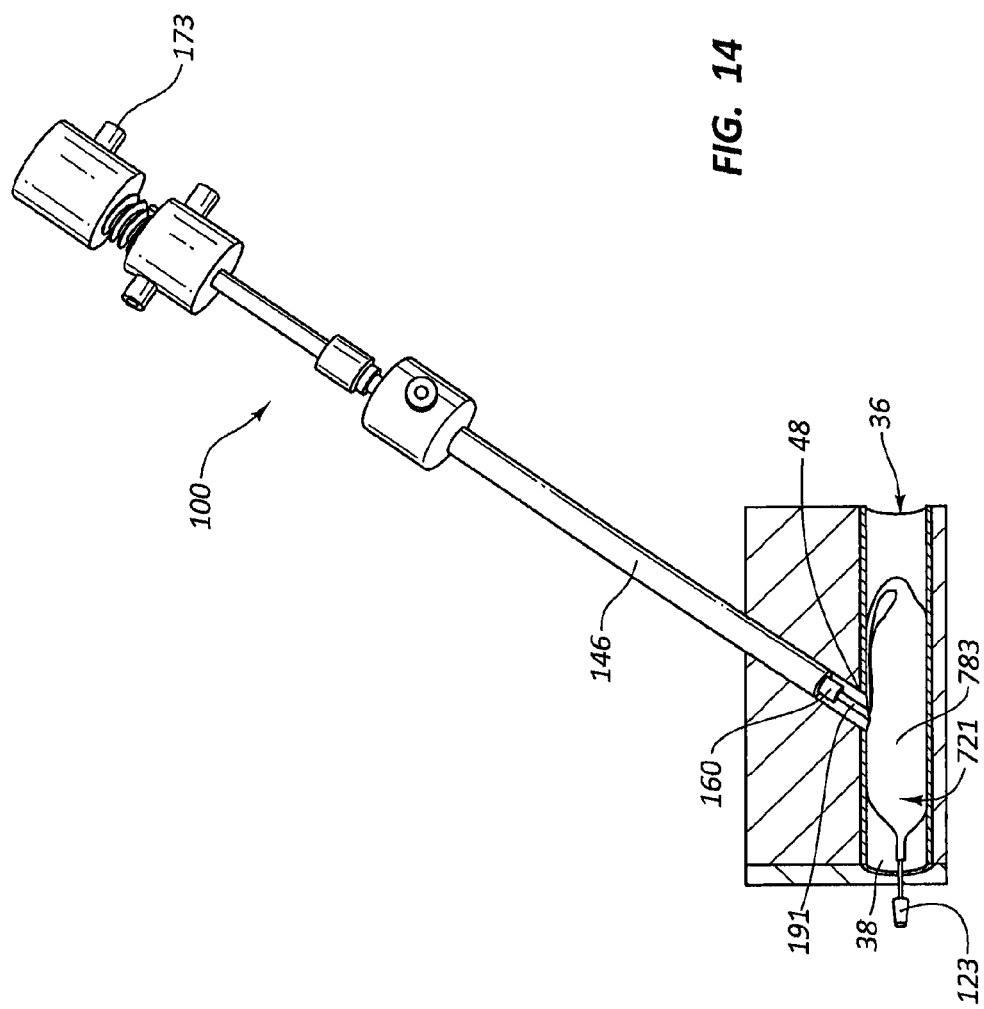

Referring to FIGS. 13 and 14, the sealing system 100 includes another exemplary embodiment of a temporary expandable member 721 including a tube 783 that is positioned within blood vessel 36. Tube 783 is pressurized through hub 173. During pressurization of tube 783, the tube 783 expands in a radial and longitudinal direction. The more pressure that is applied to tube 783, the more the expandable member covers the percutaneous puncture 48. As seen in FIG. 14, tube 791 acts as a support member within the sealing material. During the removal of the temporary expandable member 721, a channel within the sealing material that is positioned outside the blood vessel 36 adjacent to the percutaneous puncture 48 may become compromised or damaged. Tube 791 may help provide support and protect the sealing material while the temporary expandable member 721 is withdrawn through tube 191.

Figure 15:
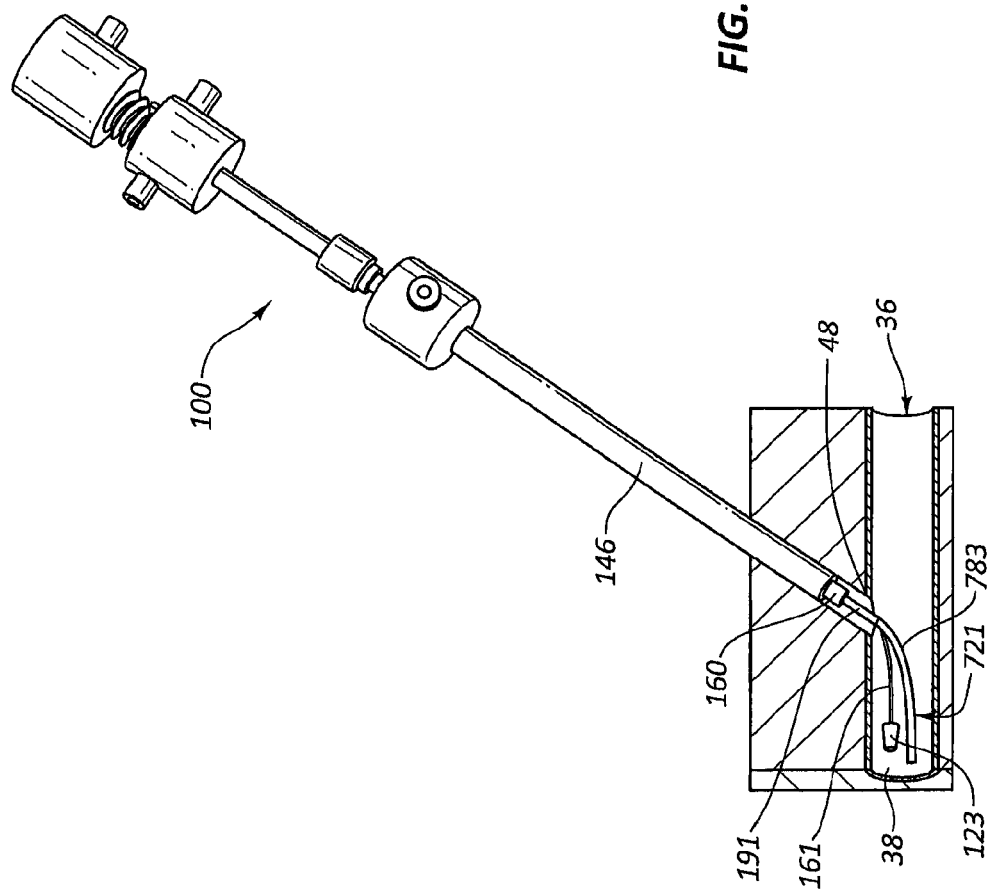
FIG. 15 illustrates an exemplary embodiment of a detachable tip and a support wire exiting a tube.

Referring to FIG. 15, the detachable tip 123 and support wire 161 are shown exiting tube 191. A temporary expandable member 721 is deflated and removed through tube 191. Tube 191 may be retracted into delivery tube 160. Detachable tip 123 may be retracted up against the distal end of delivery tube 160 or tube 191. The detachable tip 123 is released from support wire 161 (e.g., by contact with the distal end of delivery tube 160 or tube 191) and is positioned within the first stage sealing material.

Prior to separation of the detachable tip 123, the success of the closure may be evaluated. The detachable tip 123 may be positioned next to delivery tube 160 within the first stage sealing material. The guide sheath 46 and sealing system 100 may be removed. The tissue tract may be evaluated for any bleeding. If no sign of bleeding, the guide sheath 146 and sealing system 100 may be advanced over support wire 161 and the detachable tip 123 may be released within the first stage sealing material. The support wire 161 may act as a rail to help position devices back through the arteriotomy and stop bleeding if a successful closure does not occur.

Figure 16:
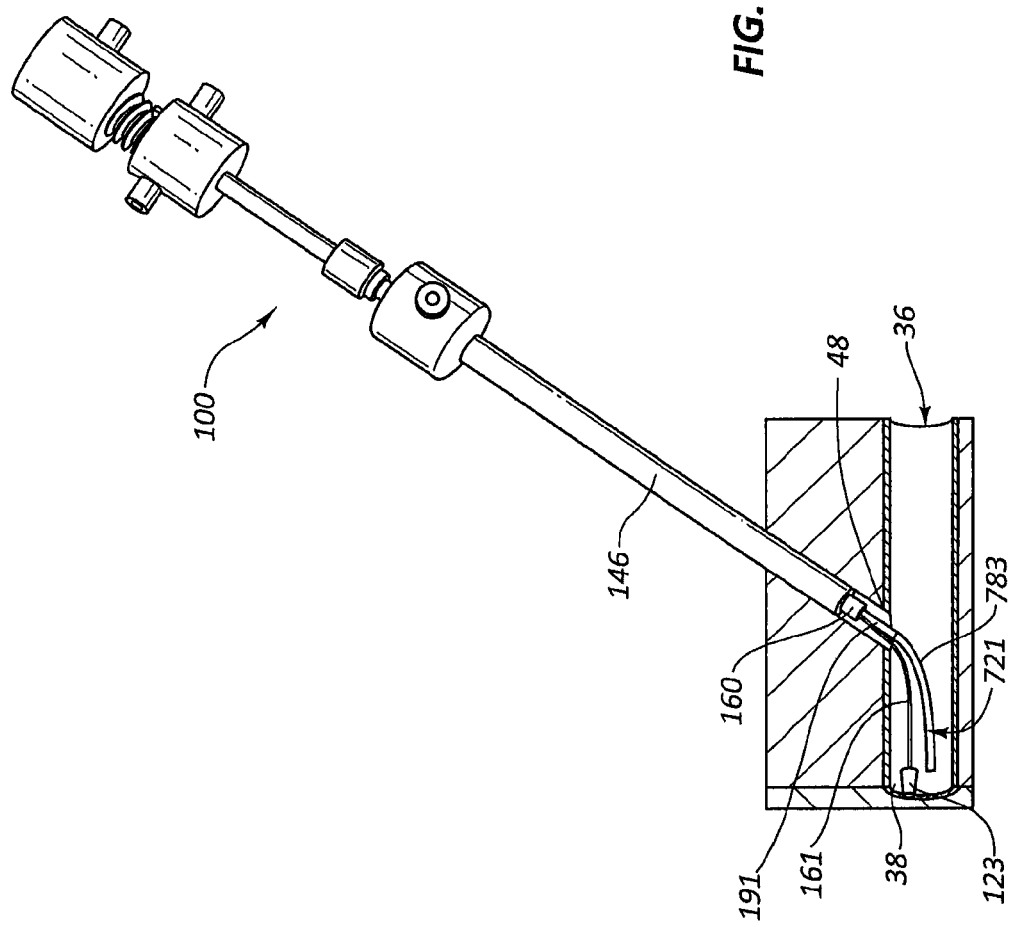
FIG. 16 illustrates an exemplary embodiment of a detachable tip and a support wire exiting a delivery tube.

Referring to FIG. 16, the detachable tip 123 and support wire 161 are shown exiting the delivery tube 160. Temporary expandable member 721 is deflated and removed through tube 191. Tube 191 is retracted up to delivery tube 160. Detachable tip 123 and support wire 161 may be retracted up against the distal end of delivery tube 160. The detachable tip 123 is released from support wire 161 and is positioned within the first stage sealing material 167.

Figure 17:
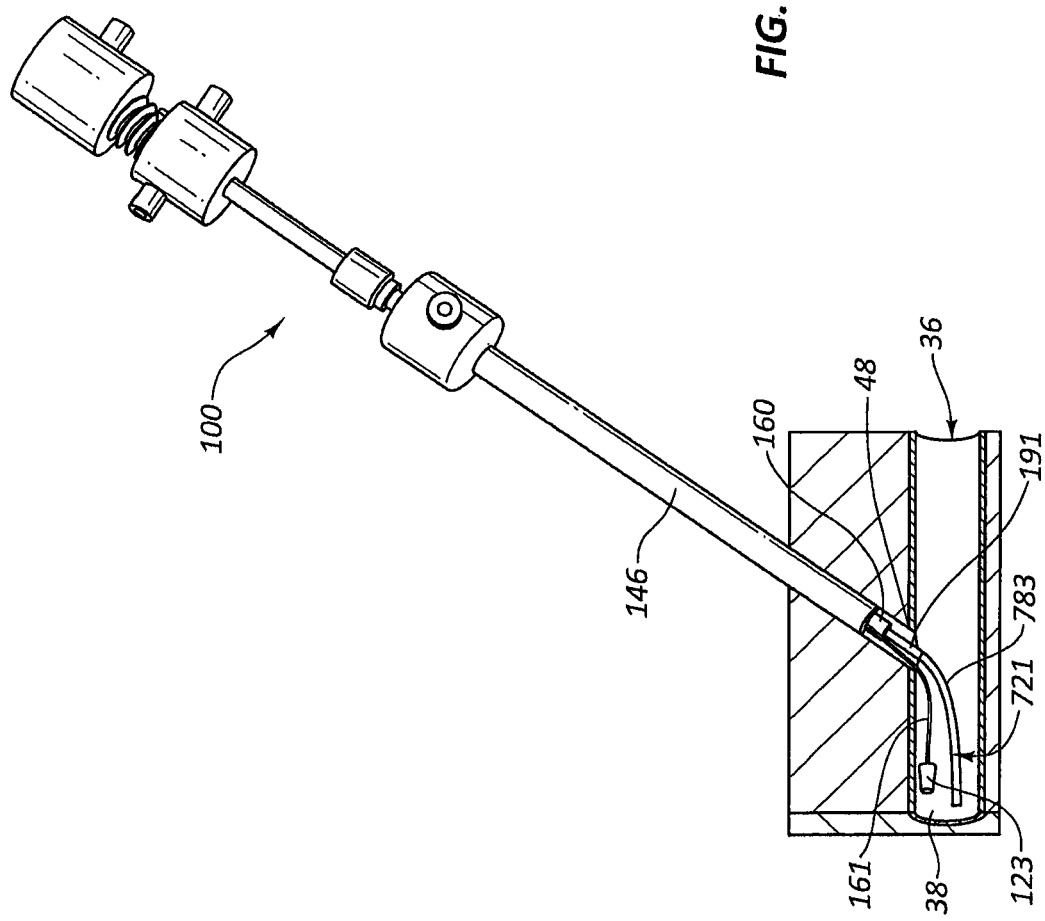
FIG. 17 illustrates an exemplary embodiment of a detachable tip and a support wire exiting a guide sheath.

Referring to FIG. 17, the exemplary embodiment of detachable tip 123 and support wire 161 is shown exiting the guide sheath 146. Temporary expandable member 721 is deflated and removed through tube 191. Tube 191 is retracted up to delivery tube 160. Detachable tip 123 and support wire 161 are retracted up against the distal end of the guide sheath 146. The detachable tip 123 is released from support wire 161 and is positioned within the first stage sealing material 167.

Figure 18:
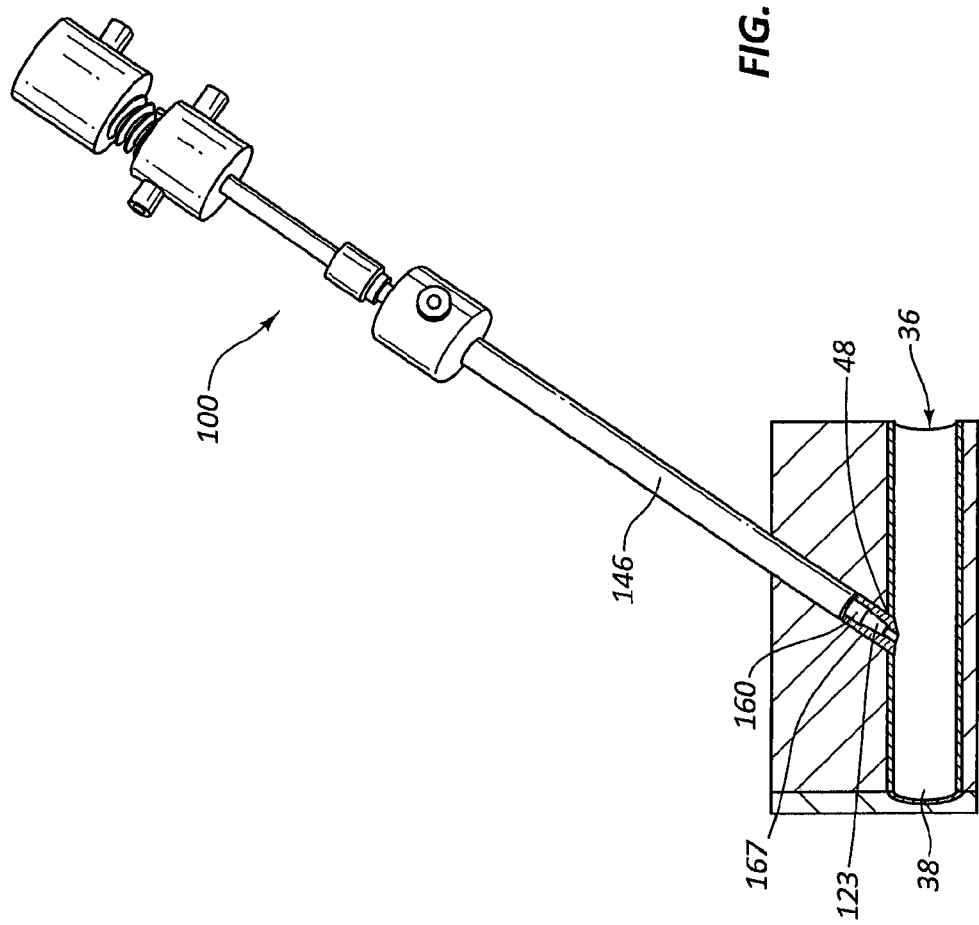
FIG. 18 illustrates an exemplary embodiment of a detachable tip delivered through a delivery tube.
Figure 19:
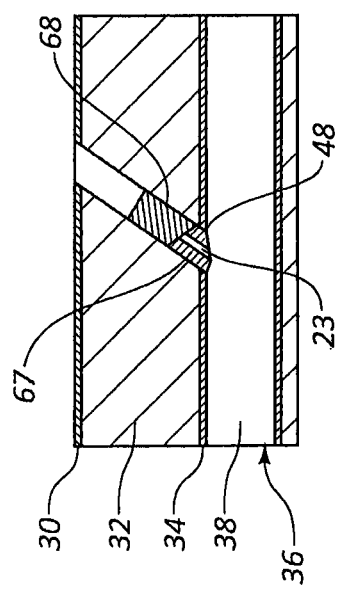
FIG. 19 illustrates an exemplary embodiment of first and second stage sealing materials and a detachable tip positioned over a percutaneous puncture.

Referring to FIG. 18, the detachable tip 123 is shown delivered after the first stage sealing material 167 is delivered. The first stage sealing material 167 is delivered and positioned next to percutaneous puncture 48. The temporary expandable member 721 is removed through delivery tube 160. A detachable tip 123 is inserted into the proximal end of delivery tube 160 and is pushed down the delivery tube lumen until detachable tip 123 exits the distal end of delivery tube 160. Once the detachable tip 123 is positioned within the first stage sealing material, the second stage sealing material may be delivered. The sealing system 100 and guide sheath 46 are removed and the closure is completed as shown in FIG. 19.

Figure 20:
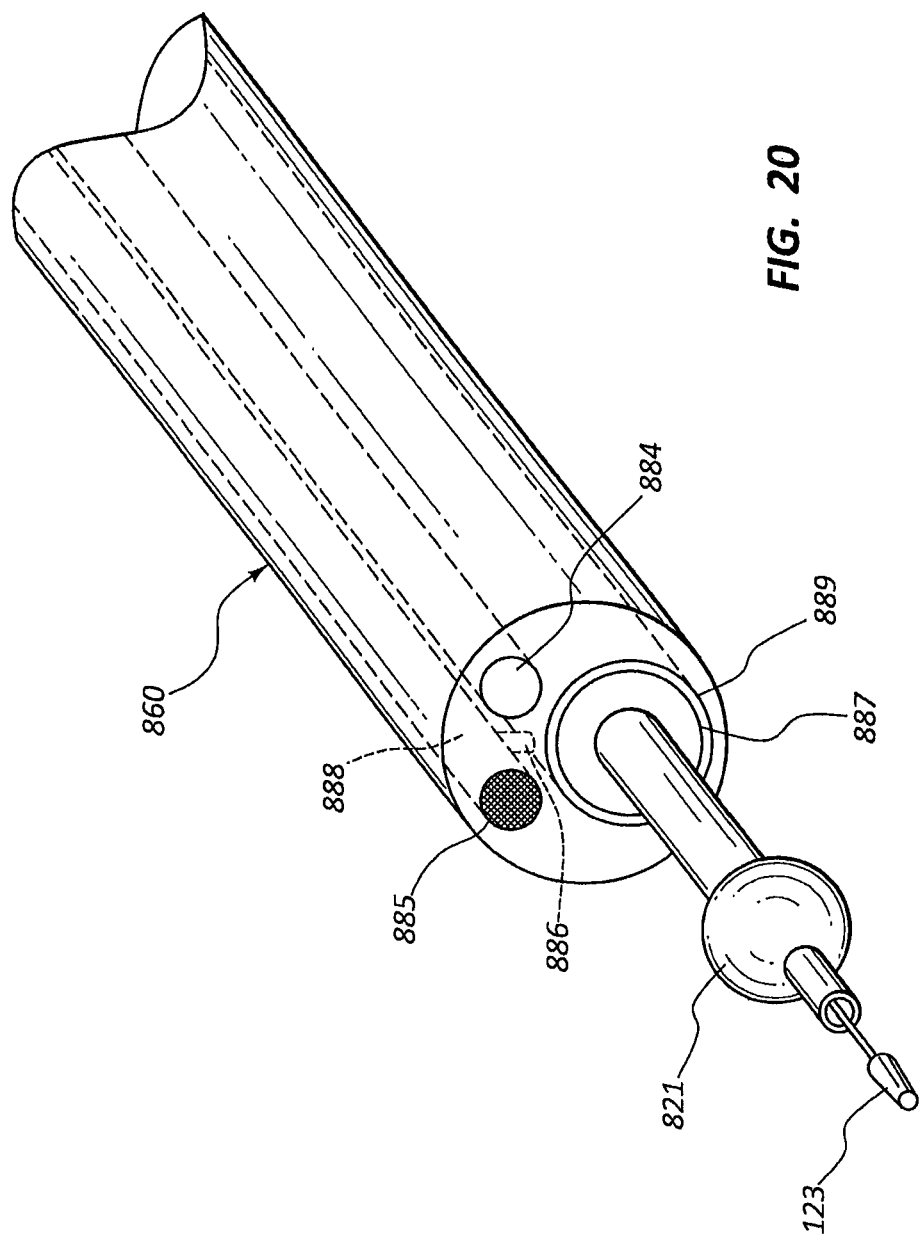
FIG. 20 illustrates an exemplary embodiment of a sealing material delivery tube with a side lumen.

Referring to FIG. 20, the exemplary embodiment illustrates a device for use in restricting first stage sealing material from entering a delivery lumen that is used to deliver the second stage sealing material. The device may be part of one of the sealing system 100 embodiments described above. The device may include a delivery tube 860 having three lumens: a temporary expandable member shaft lumen 889, a first stage sealing material delivery lumen 884, and a second stage sealing material delivery lumen 888.

The first stage sealing material is delivered through delivery lumen 884 and is unable to enter lumen 889 and delivery lumen 888. Delivery lumen 888 has a bypass channel 886 that communicates with lumen 889. The distal end of delivery lumen 888 may be closed with, for example, a plug 885. A shaft of a temporary expandable member 821 covers the opening into bypass channel 886 thereby restricting movement of first stage sealing material into the delivery lumen 888. Delivering the second stage sealing material may include removing the temporary expandable member 821 from lumen 889. The removal of temporary expandable member 821 opens up the bypass channel 886 and allows the delivery of the delivery lumen 888.

Figure 21:
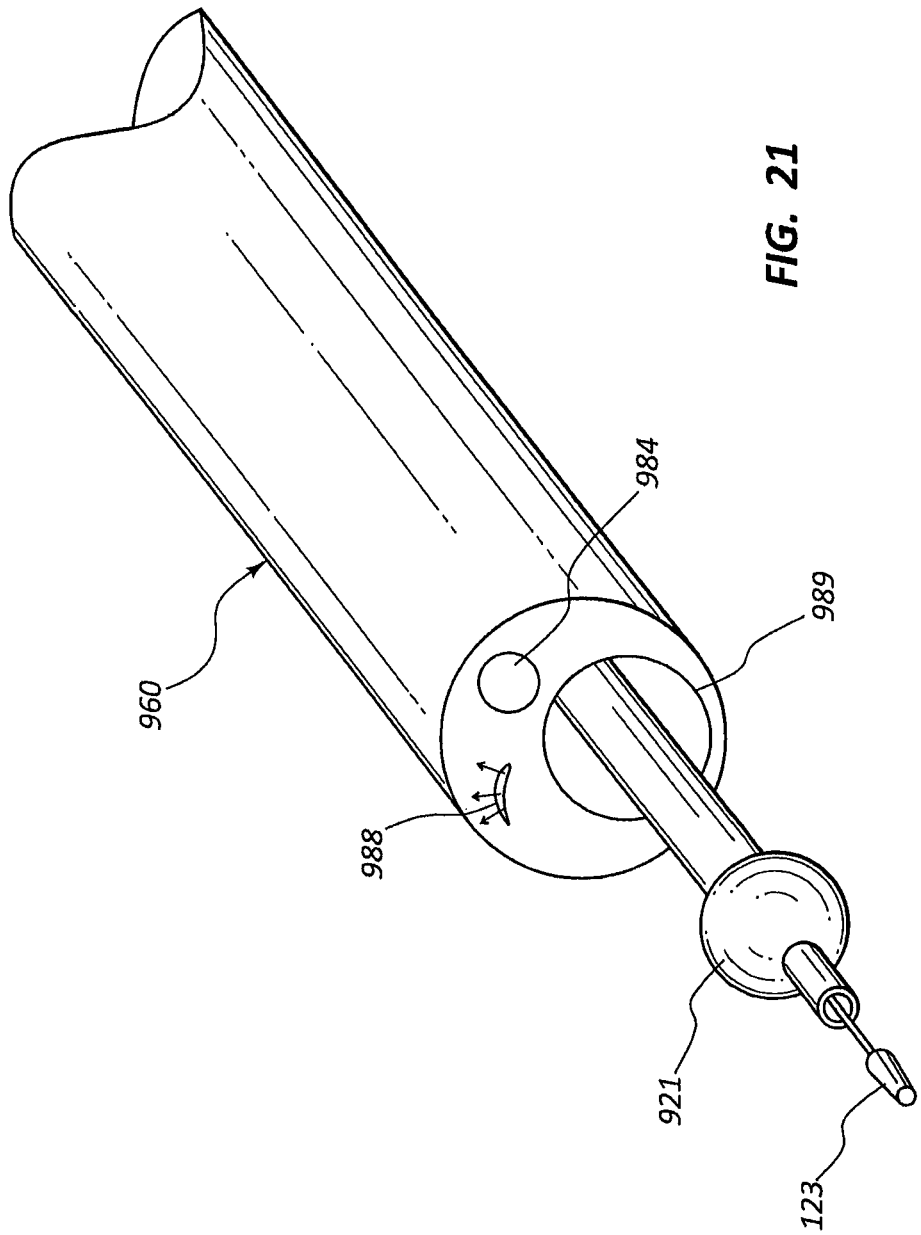
FIG. 21 illustrates an exemplary embodiment of a sealing material delivery tube with a one way valve.

Referring to FIG. 21, the exemplary embodiment illustrates another device for use in restricting first stage sealing material from entering a lumen that is used to deliver the second stage sealing material. The device may include a delivery tube 960 having three lumens: a temporary expandable member shaft lumen 989, a first stage sealing material delivery lumen 984, and a second stage sealing material delivery lumen 988. The temporary expandable member shaft lumen 989 is configured to receive a temporary expandable member 921. The first stage sealing material is delivered through delivery lumen 984 and is unable to enter delivery lumen 988. The distal end of delivery lumen 988 is collapsed and is sealed to restrict movement of first stage sealing material into delivery lumen 988. The collapsed distal end of delivery lumen 988 acts as a one way valve that is sealed during the delivery of first stage sealing material and opens when the second stage sealing material is delivered down delivery lumen 988. The distal end of delivery lumen 988 may be made of a lower durometer polymer (i.e., softer) that allows the distal end to open during the injection of the second stage sealing material through delivery lumen 988.

Figure 22:
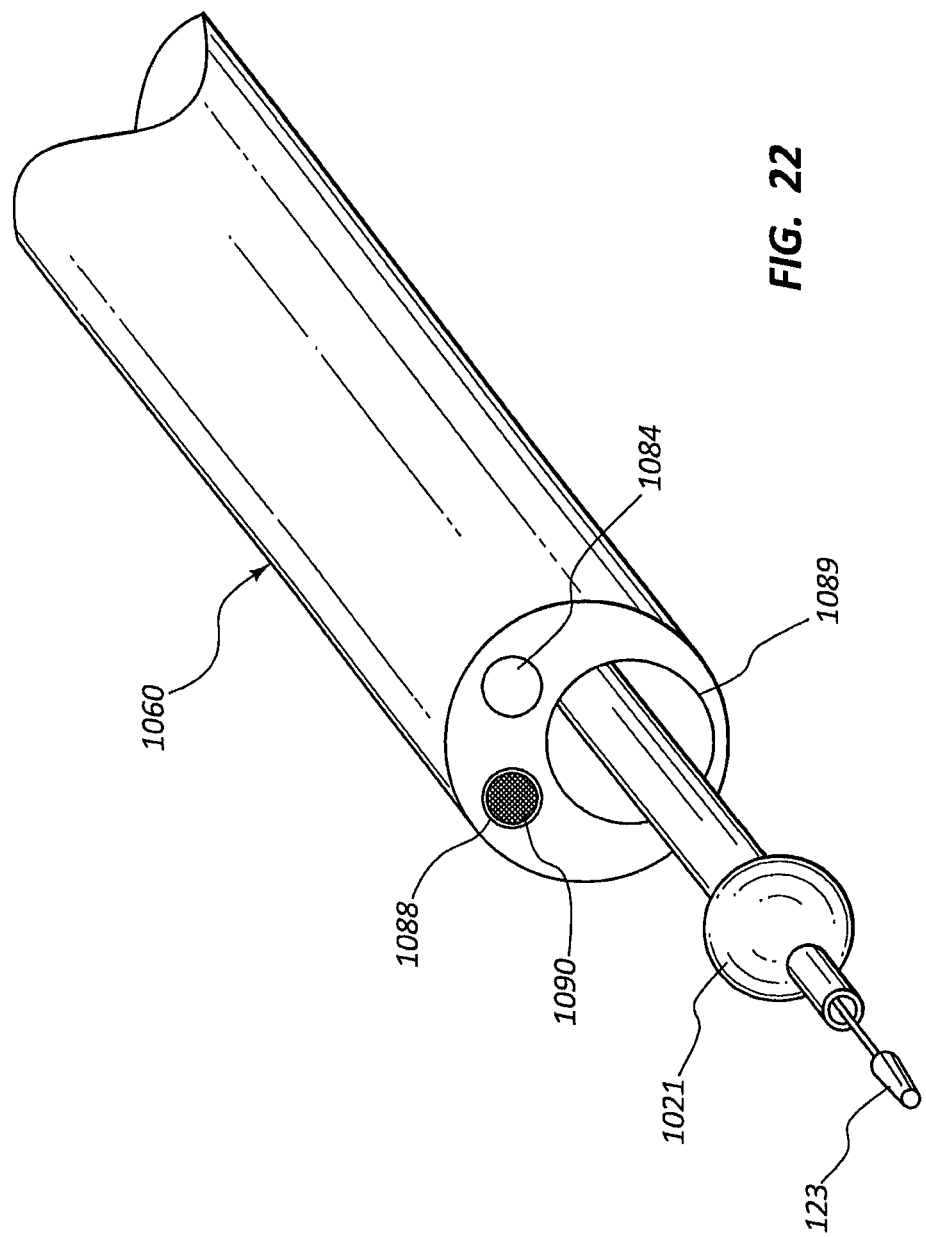
FIG. 22 illustrates an exemplary embodiment of a sealing material delivery tube with a mandrel blocking a delivery lumen.

Referring to FIG. 22, the exemplary embodiment illustrates another device for use in restricting first stage sealing material from entering the lumen that is used to deliver the second stage sealing material. The device may include a delivery tube 1060 includes three lumens: a temporary expandable member shaft lumen 1089, a first stage sealing material delivery lumen 1084, and a second stage sealing material delivery lumen 1088. The first stage sealing material is delivered through delivery lumen 1084 and is unable to enter delivery lumen 1088. The distal end of delivery lumen 1088 is plugged by a removable structure such as a mandrel 1090 that seals the distal end of delivery lumen 1088. Prior to the delivery of second stage sealing material, mandrel 1090 is removed from the proximal end of delivery lumen 1088. The removal of mandrel 1090 opens the delivery lumen 1088 and allows the second stage sealing material to be delivered.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vessel puncture closure device, comprising:
   a delivery device;
   an expandable member configured to advance through the delivery device and through a vessel puncture in a vessel, the expandable member being operable to temporarily seal closed the vessel puncture from within the vessel;
   a first sealing material deliverable through the delivery device to the vessel puncture to seal closed the vessel puncture from outside the vessel;
   a guide wire having a distal end portion;
   a detachable sealing tip mounted to the distal end portion of the guide wire at a location distal of the expandable member and being configured to detach from the guide wire within the first sealing material after removing the expandable member through the first sealing material.

2. The vessel puncture closure device of claim 1, wherein the guide wire extends through the expandable member.

3. The vessel puncture closure device of claim 1, wherein the guide wire extends through the delivery device outside of the expandable member.

4. The vessel puncture closure device of claim 1, wherein the expandable member includes first and second balloon members, the first balloon member being configured to restrict blood flow through a vessel and the second balloon member is configured to temporarily seal closed the vessel puncture from within the vessel.

5. The vessel puncture closure device of claim 1, wherein the expandable member includes first and second balloon members arranged overlapping the vessel puncture within the vessel.

6. The vessel puncture closure device of claim 1, wherein the delivery device includes a delivery tube comprising: an expandable member shaft lumen configured to receive the expandable member, a first stage sealing material delivery lumen configured to deliver the first sealing material, and a second stage sealing material delivery lumen configured to deliver a second sealing material.

7. The vessel puncture closure device of claim 6, wherein the second stage sealing material delivery lumen includes a one-way valve positioned at a distal end portion thereof that restricts flow of the first sealing material into the second stage sealing material delivery lumen.

8. The vessel puncture closure device of claim 6, further comprising a mandrel positioned in the second stage sealing material delivery lumen and removable after the first sealing material has been delivered through the first stage sealing material delivery lumen and before delivering the second sealing material through the second stage sealing material delivery lumen.

9. The vessel puncture closure device of claim 6, further comprising a bypass channel formed between the second stage sealing material delivery lumen and the expandable member shaft lumen, the expandable member sealing closed the bypass channel to restrict flow of the second sealing material until after the expandable member is retracted proximal of the bypass channel.

10. The vessel puncture closure device of claim 1, wherein the expandable member blocks blood flow through the vessel when operated to temporarily seal closed the vessel puncture from within the vessel.

11. A method of closing a puncture in a vessel, comprising:
    providing a puncture closure device including a delivery device, an expandable member, a first sealing material, a guide wire, and a detachable sealing tip mounted to a distal end of the guide wire at a location distal of the expandable member;
    advancing a delivery device to the puncture;
    advancing the expandable member through the delivery device and the puncture and into the vessel;
    temporarily sealing closed the puncture with the expandable member from within the vessel;
    delivering the first sealing material through the delivery device to the puncture to seal closed the puncture from outside the vessel;
    removing the expandable member through the first sealing material;
    depositing the detachable sealing tip within the first sealing material.

12. The method of claim 11, further comprising advancing the guide wire through the vessel puncture to position the detachable sealing tip within the vessel before advancing the expandable member through the delivery device and into the vessel.

13. The method of claim 12, wherein depositing the detachable sealing tip within the first sealing material includes retracting the guide wire through the first sealing material after removing the expandable member through the first sealing material.

14. The method of claim 11, wherein depositing the detachable sealing tip includes advancing the guide wire through the delivery device to the first sealing material after removing the expandable member through the first sealing material.

15. The method of claim 11, further comprising delivering a second sealing material through the delivery device to the first sealing material after removing the expandable member through the first sealing material.

16. The method of claim 15, wherein the delivery device includes at least first and second lumens, and delivering the first sealing material includes advancing the first sealing material through the first lumen, and delivering the second sealing material includes advancing the second sealing material through the second lumen.

17. The method of claim 11, wherein the expandable member includes first and second balloon members, the method including operating the first balloon members to temporarily seal closed the vessel puncture, and operating the second balloon member to temporarily stop blood flow through the vessel.

18. The method of claim 11, further comprising temporarily blocking blood flow through the vessel with the expandable member.

* * * * *